(12) United States Patent
Tooren et al.

(10) Patent No.: US 11,129,920 B2
(45) Date of Patent: Sep. 28, 2021

(54) TISSUE-ADHESIVE BIOMEDICAL MATERIALS

(71) Applicant: Polyganics IP B.V., Groningen (NL)

(72) Inventors: Martin Franke Tooren, Bedum (NL); Dirk Erik Muller, Assen (NL); Justin Van Der Veen, Marum (NL)

(73) Assignee: Polygames IP B.V., Groningen (NL)

( * ) Notice: Subject to any disclaimer, the term of this patent is extended or adjusted under 35 U.S.C. 154(b) by 0 days.

(21) Appl. No.: 16/089,610

(22) PCT Filed: Mar. 31, 2017

(86) PCT No.: PCT/NL2017/050202
§ 371 (c)(1),
(2) Date: Sep. 28, 2018

(87) PCT Pub. No.: WO2017/171551
PCT Pub. Date: Oct. 5, 2017

(65) Prior Publication Data
US 2020/0254137 A1  Aug. 13, 2020

(30) Foreign Application Priority Data
Mar. 31, 2016  (NL) .................................... 2016527

(51) Int. Cl.
*C09J 175/06* (2006.01)
*A61L 24/04* (2006.01)
(Continued)

(52) U.S. Cl.
CPC ......... *A61L 24/046* (2013.01); *A61L 24/0042* (2013.01); *A61L 31/06* (2013.01);
(Continued)

(58) Field of Classification Search
CPC ...... C08G 18/348; C08G 18/73; C08G 18/10; C09J 175/06; A61L 24/046; A61L 24/0042; A61L 31/06; A61L 31/148
See application file for complete search history.

(56) References Cited

U.S. PATENT DOCUMENTS 6,784,273 B1 * 8/2004 Spaans .................... A61L 27/18
528/65
2006/0008419 A1 * 1/2006 Hissink ............... A61L 24/0036
424/45

(Continued)

FOREIGN PATENT DOCUMENTS

CN          1205733 A     1/1999
CN          1365378 A     8/2002
(Continued)

OTHER PUBLICATIONS

Szycher's Handbook of Polyurethanes. Szycher. Jul. 13, 2012.*
(Continued)

*Primary Examiner* — Michael L Leonard
(74) *Attorney, Agent, or Firm* — Banner & Witcoff, Ltd.

(57) ABSTRACT

The invention is directed to a biodegradable tissue-adhesive polyurethane polymer comprising at least one amorphous segment and at least one polyurethane segment, wherein at least one of said polyurethane segment comprises a tissue-reactive functional group. A further aspect of the invention is directed to biodegradable tissue-adhesive medical devices, based on the polyurethane polymer, having the structure of a sheet, foam, stent, tube or gel. The polyurethane polymer and the device can be used in medical application.

15 Claims, 2 Drawing Sheets

(51) Int. Cl.
    *C08G 18/34*   (2006.01)
    *A61L 24/00*   (2006.01)
    *A61L 31/06*   (2006.01)
    *A61L 31/14*   (2006.01)
    *C08G 18/10*   (2006.01)
    *C08G 18/73*   (2006.01)

(52) U.S. Cl.
    CPC ............ *A61L 31/148* (2013.01); *C08G 18/10* (2013.01); *C08G 18/348* (2013.01); *C08G 18/73* (2013.01); *C09J 175/06* (2013.01); *C08G 2170/00* (2013.01); *C08G 2230/00* (2013.01)

(56) References Cited

U.S. PATENT DOCUMENTS

| 2006/0188547 | A1  | 8/2006 | S. Bezwada |
| 2011/0123476 | A1* | 5/2011 | Kapiamba ............... A61L 24/04 424/78.06 |
| 2014/0248232 | A1  | 9/2014 | Hong et al. |

FOREIGN PATENT DOCUMENTS

| CN | 101816801 A | 9/2010 | |
| WO | WO-2009064861 A2 * | 5/2009 | ............ A61L 27/18 |
| WO | 2013/095138 A1 | 6/2013 | |

OTHER PUBLICATIONS

Adelmeijer, J. et al., "In vitro effects of proteases in human pancreatic juice on stability of liquid and carrier-bound fibrin sealants," British Journal of Surgery, Jun. 26, 2013; 100: pp. 1498-1504, John Wiley & Sons Ltd.

Simo, K.A. et al., "Hemostatic Agents in Hepatobiliary and Pancreas Surgery: A Review of the Literature and Critical Evaluation of a Novel Carrier-Bound Fibrin Sealant (TachoSil)," International Scholarly Research Network ISRN Surgery, Jul. 24, 2012, vol. 2012, pp. 1-12.

Excerpts from Szycher's Handbook of Polyurethanes (2013, CRC press).

* cited by examiner

TISSUE-ADHESIVE BIOMEDICAL MATERIALS

RELATED APPLICATIONS

This application is a National Stage Application under 35 U.S.C. 371 of PCT application PCT/NL2017/050202 designating the United States and filed Mar. 31, 2017; which claims the benefit of NL application number 2016527 and filed Mar. 31, 2016 each of which are hereby incorporated by reference in their entireties.

The invention is directed to polyurethanes for medical applications. The invention is particularly directed to biodegradable polyurethanes and medical devices thereof that have tissue-adhesive properties.

Polyurethanes find a wide range of biomedical application due to their favorable mechanical properties, such as biodegradability, biocompatibility, mechanical strength and handling flexibility in processing them into variously shaped and structured devices. Examples of polyurethane for medical applications include nasal dressings, nerve guides, meniscal reconstruction materials, artificial skins and hemostatic sponges.

For a number of these applications, it may be required that the surgeon fixates the device in the patient's body. This is typically achieved by mechanical fixation such as stapling and/or suture.

It is desirable to replace or complement the mechanical fixation by adhesive fixation provided by the device itself. Moreover, besides the beneficial effects of tissue-adhesiveness for present applications, it may also open new applications for polyurethane and devices thereof. It is thus highly desirable for the polyurethanes to be tissue-adhesive.

Moreover, it is desirable that the tissue-adhesive materials are resistant to bile and other (acidic) bodily fluids. As such, the tissue-adhesive materials can be used to prevent or limit intra and post-surgical bleeding and leakage of bodily fluids. For instance, after hepatobiliary and pancreatic surgery, bleeding and loss of other fluid is still a problem for which improved sealant materials are desired.

WO2011/079336 describes a hemostatic sponge, available under the tradename Hemopatch™, that is based on a blend of biological polymers such as collagen, gelatin, fibrin or polysaccharides blended with a tissue-adhesive polymer such polyethylene glycol that is functionalized with N-hydroxysuccinimide-esters. The biological polymers face the drawback of not being sufficiently water resistant. This means that they rapidly hydrolyze and degrade after application as well as that, in particular upon exposure to water, they lack the favorable mechanical properties of polyurethane.

Other tissue-adhesives, e.g. those available under the tradename Tachosil™ (from Takeda) are based on fibrin of both of human an animal origin. Fibrin based glues are difficult to manufacture and use human and/or animal blood as a fibrin source, entailing the potential risk of transferring diseases and eliciting undesired, and fatal immune responses. Moreover, fibrin-based sealants such as Tachosil™ are ineffective in reducing postoperative resection surface related complications such as leakage, bleeding and abscess formation. Therefore, routine use of fibrin sealants is not recommended.

It is desired to combine the favorable mechanical properties of polyurethanes with tissue-adhesive properties.

BRIEF DESCRIPTION OF THE DRAWINGS

The foregoing and other features and advantages of the present embodiments will be more fully understood from the following detailed description of illustrative embodiments taken in conjunction with the accompanying drawings in which.

The present invention provides a biodegradable tissue-adhesive polyurethane polymer comprising at least one amorphous segment and at least one polyurethane segment, wherein at least one of said polyurethane segment comprises a tissue-reactive functional group.

The presence of the amorphous segment and the polyurethane segment provides the favorable mechanical properties of polyurethane polymer. The present invention thus provides a polyurethane polymer that may provide both tissue-adhesive properties as well as structure-providing properties.

The term "structure-providing properties" is used to indicate that the polyurethane polymer as such may function in a device as tissue support, fluid absorbance, tissue sealing (e.g. treatment or prevention of fluid/air leakage after surgery), and the like. It is thus not required to blend the polyurethane polymer with an additional polymer for the structure providing properties, as is for instance the case in two-components-based tissue adhesive materials, as for instance described in WO2009/019516, wherein a device available under the trade name TissuePatch™ is disclosed.

The tissue-adhesive properties originate inter alia from the tissue-reactive functional group. With tissue-reactive functional group is meant any chemical group, functionality or moiety that may react with tissue and form e.g. a covalent bond. Cells (and thus the tissue that is formed by cells) typically comprises protein and carbohydrates on the outer surface that may react in a variety of reactions. The present invention is thus based on the idea that the polyurethane polymer reacts with the tissue and a covalent bond is formed. For instance, amines of proteins may react with activated ester to form amide bonds or a sulfide may react with another sulfide to form a disulfide bond. It may be appreciated that other bonding types, such as Van-der-Waals interactions, hydrogen bonding, ionic interaction and the like, may also play a role in the overall bonding capacity of the polyurethane polymer of the present invention. The specific occurrence and strength of each type of bonding generally depends on the type of tissue, the chemical composition of the polyurethane polymer and the structure of the device based thereon.

The tissue-reactive functional group is appropriately stable in aqueous environment, but at the same time sufficiently reactive with respect to the tissue. As such, preferred polyurethane polymers in accordance with the present invention comprise a tissue-reactive functional group that is a carboxylic acid, an activated ester, an acid chloride, an anhydride, an aldehyde, p-nitrophenyl carbonate, epoxide, an isocyanate, vinyl sulfone, maleimide, o-pyridyl-disulfide, a thiol or combinations thereof. Activated esters, acid chlorides, anhydrides, aldehydes, vinyl sulfone, maleimide and isocyanates are electrophilic groups that may typically react with an amine or other nucleophile of the tissue. Thiol or o-pyridyl-disulfide may form a disulfide bond with the tissue.

Particularly preferred as the tissue-reactive functional group are activated esters. The activated ester may be a thioester, a perfluoroalkyl ester, a pentafluorophenol ester, a N-hydroxysuccinimide (NHS) ester, derivatives thereof, as well as combinations of these. Particularly good results have been obtained with N-hydroxysuccinimide ester, as this ester is stable enough to allow easy handling but also allows a good tissue-bonding. N-hydroxysuccinimide ester or derivatives thereof is therefore most preferred. Examples of derivatives of NHS ester are N-hydroxysulfosuccinimide and salts thereof.

The amorphous segment in accordance with the present invention is typically a (co-)polyester, such as poly(lactide-co-caprolactone) and/or a (co-)polyether such as polyethylene glycol. In particular with respect to the amorphous segment, reference is made to WO99/64491 and WO2004/062704, which are both incorporated herein in their entirety.

WO99/64491 describes a phase separated polyurethane polymer comprising an amorphous segment. Like for the amorphous segment in accordance with the present invention, the segment described therein is typically based on a polyester, preferably a random co-polyester, obtainable by ring-opening polymerization. The polyester is preferably based on lactic acid, succinic acid, diethylene glycol, 1,4-butanediol, 1,6-hexanediol and/or diethylene glycol. The random co-polyester is preferably a co-polyester of lactide, glycolide, trimethylene carbonate and/or ε-caprolactone. More preferably, the random co-polyester is a based on lactide and ε-caprolactone containing 5 to 95%, preferably 40 to 60% of units of lactide and 5 to 95%, preferably 40 to 60% of units of ε-caprolactone, based on number.

In a particular embodiment of the present invention, the amorphous segment comprises a hydrophilic segment. Examples of amorphous segments comprising hydrophilic segments are described in WO2004/062704. The presence of the hydrophilic segment increases the absorption capacities of the device based on the polyurethane polymer and may also influence the rate of biodegradation. The hydrophilic segment may for instance be derived from polypeptide, poly(vinyl alcohol), poly(vinylpyrrolidone), poly(hydroxymethylmethacrylate) or polyethers. A hydrophilic segment is preferably a polyether such as poly(ethylene glycol). It should be appreciated that the hydrophilic segments are appropriately inert towards the tissue-reactive functional group, which is to say that they do not, or do not substantially react chemically with the tissue.

The term "amorphous" as used herein, refers to segments present in the polyurethane polymer of the invention with at least one glass transition temperature below the temperature of the human or animal body for which the polyurethane polymer is intended to be used, and may also refer to a combination of an amorphous and crystalline segment which is completely amorphous when packed in the human or animal body. For example, PEG in a pre-polymer may be crystalline in pure form, but may be amorphous when comprised in the polyurethane polymer of the invention. Longer PEG segments may even be partly crystalline, at least in part, when comprised in the polyurethane polymer, but will become amorphous ("dissolves") when placed in contact with water.

The term "segment" as used herein, refers to a polymeric structure of any length. In the art of polymer technology a long polymeric structure is often referred to as a block, whereas a short polymeric structure is often referred to as a segment. Both these conventional meanings are understood to be comprised in the term "segment" as used herein.

The tissue-adhesive polyurethane polymer in accordance with the present invention is biodegradable. The term "biodegradable" as used herein, refers to the ability of a polymer to be acted upon biochemically in general by living cells or organisms or part of these systems, including hydrolysis, and to degrade and disintegrate into chemical or biochemical products. Preferably, the polyurethane polymer is also bioresorbable meaning that the materials can be broken down by and be cleared from the body, without requiring mechanical removal.

The polyurethane segment is based on building blocks (e.g. monomers or pre-polymers) that are connected by urethane bonds (—N(R)C(=O)O—). These bonds are typically obtainable by reacting isocyanates (—NCO) and alcohols (—OH). The polyurethane polymer is thus typically based on building blocks comprising (di)isocyanate or (di)alcohol functionalities.

In a particular embodiment of the present invention, the polyurethane polymer may be of the formula $$\{-Q-R'-Q-R-Q-R'-Q-(R^f)_n-\!\!\!\!\!\!\!-\!\!\!\!\!\!\!-(R^e)_m-\}_p- \qquad (I)$$

wherein R is one or more aliphatic polyesters, polyether esters, polyethers, poly(anhydrides) and/or polycarbonates and at least one R comprises an amorphous segment that optionally comprises a hydrophilic segment; R' is a $C_2$-$C_8$ alkylene, optionally substituted with $C_1$-$C_{10}$ alkyl or $C_1$-$C_{10}$ alkyl groups substituted with halides or protected S, N, P or O moieties and/or comprising S, N, P or O in the alkylene chain; $R^f$ is a functionalized chain extender substituted with the tissue-reactive functional group; $R^e$ is a chain extender, Q is an urethane bond; p is an integer from 5-500; n plus in equal 1; and n is not 0, preferably n/m is at least 0.5, more preferably at least 0.75, most preferably about 1.

The amorphous segment is comprised in at least one R. It may thus be appreciated that R may represent a mixture of two or more different types of aliphatic polyesters, polyether esters, polyethers, polyanhydrides and/or polycarbonates and may thus not be uniform throughout the polyurethane polymer. Furthermore, R typically represents (mixture of) pre-polymer(s) that is based on the amorphous segment obtainable by for instance ring-opening polymerization or random co-polymerization (vide supra), both leading to polydispersity or statistical distribution of the molecular composition and mass.

R may in particular be derived from the cyclic monomers lactide (L, D or LD), glycolide, ε-caprolactone, δ-valero-lactone, trimethylenecarbonate, tetramethylenecarbonate, 1,5-dioxepane-2-one, para-dioxanone, and combinations thereof. In a further preferred embodiment, R is an amorphous polyester derived from exclusively lactide and ε-caprolactone, with a molecular weight between 1000 and 4000.

As stated, R optionally comprises a hydrophilic segment and such a hydrophilic segment can very suitably be an ether segment, such as a polyether segment derivable from such polyether compounds as polyethyleneglycol, polypropylene glycol or polybutylene glycol. Also, a hydrophilic segment comprised in R may be derived from polypeptide, poly(vinyl alcohol), poly(vinylpyrrolidone) or poly(hydroxymethylmethacrylate). A hydrophilic segment is preferably a polyether such as poly(ethylene glycol), poly(propylene glycol) or poly(butylene)glycol.

In case the amorphous segment comprises a hydrophilic segment, said amorphous segment preferably comprises polyethylene glycol in a content of 1-80 wt %, more preferably 5-60 wt %, even more preferably 20-50 wt %, most preferably 50 wt %.

In a most preferred embodiment, R is about 25 wt. % lactide, about 25 wt. % ε-caprolactone and about 50 wt. % of polyethylene glycol.

In a typically embodiment of the present invention, the polyurethane polymer is based on R that is functionalized at both ends with an isocyanate group and chain extenders $R^f$ and $R^e$ independently being alcohols or diols. $R^f$ here represents a chain extender substituted with the tissue-reactive functional group. $R^e$ is a chain extender not functionalized with the tissue-reactive functional group.

The symbol "─╫─" indicates that a mixture of $R^e$ and $R^f$ may be present. A single "-Q-$(R^f)_n$─╫─$(R^e)_m$-Q-" segment may thus either contain $R^e$ or $R^f$ such that the entire polyurethane polymer contains in the "-Q-$(R^f)_n(R^e)_m$-Q-" segments on average partly $R^e$ and partly $R^f$.

$R^e$ may be present to dilute the presence of tissue-reactive functional groups within the polyurethane polymer. This dilution may be expressed by the ratio n/m wherein n represent the number of chain extenders functionalized with the tissue-reactive group and in represents the number of chain extenders not functionalized with the tissue-reactive functional group. The presence of $R^e$ is optional and $R^f$ may therefore be 0. $R^e$ may thus be complementary to $R^f$ (as indicated by the symbol "─╫─"), meaning that n and m added together equal 1.

It may be appreciated that the polyurethane polymer in accordance with the present invention always comprises the tissue-reactive functional group and as such, for the polyurethane polymer represented by formula (I), $R^f$ is always present and n is not equal to 0.

In a preferred embodiment, $R^f$ and $R^e$ independently comprise a $C_2$-$C_8$ alkylene, (poly)urethane group, (poly)ester such as (poly)caprolactone, (poly)lactide, (poly)ether such as (poly)ethylene glycol. A typical polyurethane group for $R^e$ may be based on 1,4-butanediol (BDO) and 1,4-butanediisocyanate (BDI) or BDO-BDI-BDO. The tissue-reactive functionalized chain extender ($R^f$) may be substituted with a $C_1$-$C_{10}$ hydrocarbon comprising the tissue-reactive functional group.

In general, both the functionalized chain extender ($R^f$) and the chain extender ($R^e$) may independently be based on any mono-alcohol or diol.

The length of $R^f$ and $R^e$ in the backbone of the polyurethane polymer may be the same or it may differ. A same length may be achieved for instance by basing both chain extenders on the same diol (e.g. on a extender comprising 1,4-butanediol as backbone) with the proviso that $R^f$ additionally contains the tissue-reactive functional group. In case all chain extenders ($R^f$ and $R^e$) are of a same length, the polyurethane segment is uniform in length and may accordingly be a crystalline segment.

The term "crystalline" as used herein, refers to segments, present in the polymer of the invention, that are crystalline when packed in the human or animal body, i.e., that have a melting temperature above the temperature of the cavities of the human or animal body into which the layer is packed. In case the polyurethane polymer comprises both a crystalline and an amorphous segment, the polyurethane polymer is a phase-separated polymer. Crystallinity and phase-separation of polyurethanes is for instance described in WO99/64491.

The crystallinity of the polyurethane segment may be influence by the structural differences of $R^e$ and $R^f$ as well as the ratio (n/m) of these chain extenders.

Typically, the polyurethane polymer of the present invention is based on a pre-polymer and one or more chain extenders, wherein at least one chain extender is substituted with the reactive functional group. The pre-polymer typically comprises or consists of the amorphous segment. Moreover, for the preparation of the polyurethane polymer, the pre-polymer is typically end-capped with isocyanates (e.g. isocyanates-based R') such that it may be chain extended by chain extenders comprising diols. It is preferred that during this chain extension, the chain extender that is indented to become the functionalized chain extender ($R^f$), is not yet substituted with the tissue-reactive functional group since chain extension conditions are generally too harsh for such groups.

It is therefore preferred that the tissue-reactive function group is introduced or obtained at late as possible in the preparation of the polyurethane polymer. A further aspect of the present invention is therefore a pre-functionalized biodegradable polyurethane suitable for the preparation of the polyurethane polymer according to the present invention.

Preferably, the pre-functionalized polyurethane polymer is of the formula $$\mathrm{\text{─}Q\text{-}R'\text{-}Q\text{-}R\text{-}Q\text{-}R'\text{-}Q\text{-}(R^x)_n\text{─}\!\!\not\!\!\text{─}(R^e)_m\text{─}\!]_p\text{─}} \quad \text{(II)}$$

wherein R, Q, R', $R^e$, n, m and p are as defined herein above, and wherein $R^x$ is a pre-functionalized chain extender, preferably a $C_2$-$C_8$ alkylene or alkyl, at least substituted with a $C_1$-$C_{10}$ hydrocarbon comprising a carboxylic acid or (alkyl) ester thereof, nitrile, isonitrile or protected S, N, P or O.

Certain pre-functionalized polymers, e.g. those comprising $R^x$ comprising a carboxylic acid, also displays tissue-adhesion, albeit in a less extent compared to the polyurethane polymer functionalized with the tissue-reactive group. The carboxylic acid of the pre-functionalized polymer may for instance non-covalently interact with tissue (e.g. by forming ionic and/or hydrogen bonds). As such, the pre-functionalized polymer can in particular embodiment identical to the tissue-adhesive polyurethane polymer of the present invention.

In a further aspect, the present invention is directed to a method for the preparation of the pre-functionalized polyurethane polymer. The methods comprises chain extending the pre-polymer or a smaller compound (e.g. R), typically end-capped with isocyanates (e.g. R', vide supra), with the chain extender substituted with a pre-reactive functional group (e.g. $R^x$) and optionally a chain extender (e.g. $R^e$) to obtain the pre-functionalized polyurethane polymer.

Said pre-functionalized polyurethane polymer may be used in a method for the preparation of the polyurethane polymer according to the invention. This method comprises providing the pre-functionalized biodegradable polyurethane polymer followed by the conversion of the pre-reactive functional group to the tissue-reactive functional group.

In the preferred embodiment, the pre-reactive functional group is typically a carboxylic acid or (alkyl) ester thereof, nitrile, isonitrile or optionally protected S, N, P or O. The atoms S, N, P or O are optionally protected to obtain higher yields in a typical polymerization reaction wherein the urethane bond in the polyurethane are formed from diisocyanide and diol units. However, after such a polymerization reaction the protected S, N P or O may be deprotected such that the pre-functionalized group can be functionalized with the tissue-reactive functional group. Accordingly, the pre-functionalized biodegradable polyurethane polymer of formula II, wherein $R^x$ comprises SH, $NH_2$, PH or OH is also a particular embodiment of the present invention.

In a further preferred embodiment, the pre-reactive functional group is carboxylic acid or an (alkyl)ester that may be converted to the carboxylic acid under mild conditions. In this preferred embodiment, the conversion of the pre-reactive functional group to the tissue-reactive functional group comprises coupling of an alcohol (such as pentafluorophenol or N-hydroxysuccinimide) with the carboxylic acid to obtain the corresponding activated ester. Coupling of the alcohol with the carboxyl acid may be achieved by standard coupling methods making use of coupling reagents such as N,N'-dicyclohexylcarbodiimide (DCC), (benzotriazol-1-yloxy)tris(dimethylamino)phosphonium hexafluorophosphate (BOP), bis(2-oxo-3-oxazolidinyl)phosphinic chloride (BOP—Cl), (benzotriazol-1-yl-oxytripyrrolidinophosphonium hexafluorophosphate) (PyBOP), ((7-azabenzotriazol-1-yloxy)tripyrrolidinophosphonium hexafluorophosphate) (PyAOP), (2-(1H-benzotriazol-1-yl)-1,1,3,3-tetramethyluronium hexafluorophosphate) (HBTU), 1-hydroxy-7-azabenzotriazole (HOAt), hydroxybenzotriazole (HOBt), (1-[bis(dimethylamino)methylene]-1H-1,2,3-triazolo[4,5-b]pyridinium 3-oxid hexafluorophosphate) (HATU), 1-ethyl-3-(3-dimethylaminopropyl)carbocliimide (EDCI), diphenylphosphoryl azide (DPPA), (1-cyano-2-ethoxy-2-oxoethylidenaminooxy)dimethylamino-morpholino-carbenium hexafluorophosphate (COMU™), [ethyl cyano(hydroxyimino)acetato-$O^2$]tri-1-pyrroliclinylphosphonium hexafluorophosphate (PyOxim), bromotris(dimethylamino)phosphonium hexafluorophosphate (BroP), bromotripyrrolidinophosphonium hexafluorophosphate (PyBroP™), 2-chloro-1,3-dimethylimidazolidinium hexafluorophosphate (CIP) and the like. Also 4-(dimethylamino)pyridine (DMAP) may or may not be present during the coupling.

In a particular embodiment, the method for the production of the biodegradable tissue-adhesive polyurethane polymer comprises chain extending the pre-polymer with the chain extender substituted with a pre-reactive functional group and optionally a chain extender, followed by the conversion of the pre-reactive functional group to the tissue-reactive functional group.

As was described above, both the functionalized chain extender ($R^f$) (and thus also $R^x$ for that matter) as well as the chain extender ($R^e$) may independently be based on any mono-alcohol or diol. In such case, $R^f$ or $R^e$ may be an alkyl. In case the (functionalized) chain extender is based on a mono-alcohol, chain extension (and thus polymerization) will terminate with the incorporation of this mono-alcohol-based (functionalized) chain extender. By using the functionalized chain extender $R^f$ the polyurethane polymer is only terminally functionalized with the tissue-reactive function group. Thus, in a particular embodiment of the present invention, the polyurethane polymer comprises only two tissue-reactive functional groups, which groups are located on the termini of the polyurethane polymer.

In the embodiment wherein $R^f$ is a $C_2$-$C_8$ alkyl, for sake of clarity it is noted that the polyurethane polymer may also be represented by the formula (III)

wherein R, Q, R', $R^e$ and p are defined as above and $R^f$ is the alkyl functionalized with the tissue-reactive functional group. It may be appreciated that this particular representation may also be used, mutatis mutandis for embodiments wherein $R^e$ or $R^x$ are $C_2$-$C_8$ alkyl.

A further aspect of the present invention is a biodegradable tissue-adhesive medical device comprising the polyurethane polymer according to the present invention. Depending on the intended use, such device may have the structure of a sheet, foam, stent, tube or gel.

In a particular embodiment, the device in accordance with the present invention comprises additional polymers besides the polyurethane polymer. For instance, in particular when the amorphous segment of the polyurethane polymer does not comprise the hydrophilic segment, the device may comprise a hydrophilic polymer such as polyethylene glycol in a content of 1-80 wt %, more preferably 5-60 wt %, even more preferably 20-50 wt %, most preferably 50 wt %. The hydrophilic polymer can be blended with the polyurethane polymer in the device and thereby functioning similarly as the hydrophilic segment would if this was present in the amorphous segment. The advantage of separately blending a hydrophilic polymer is that different devices (i.e. with or without) the hydrophilic polymer can be produced with a single production batch of the polyurethane. This thus enables a greater flexibility in the production process.

The device of the present invention can also be a multi-layered device such as a bi-layered foam or sheet. In the multi-layered device it may be possible that only one outer layer comprises the tissue-adhesive polyurethane polymer while the other layer or layers do not comprise the tissue-adhesive polyurethane polymer. This provides the device having only one tissue-adhesive face.

In case the device has the structure of a foam, the tissue-adhesive properties of the device may be influenced by the porosity of the foam. The desired porosity of the foam may be achieved by preparing the foam from a solution of the tissue-adhesive polyurethane polymer with a specific concentration. In the embodiment wherein the device has the structure of a foam, it is preferred that the porosity of the foam is at least 90%, more preferably at least 95%.

The polyurethane polymer and devices thereof show good tissue-adhesion. The tissue-adhesion of the polymers and devices can be determined by using the following method.

Bovine liver tissue is placed inside a Teflon™ box with an opening on top. The polyurethane or device thereof is attached to a piston, for example by using double-sided tape. By using the piston, the polyurethane polymer or the device thereof is pressed onto the liver tissue at a speed of 10 mm/min until a force of 10N has been reached. At this point, the piston with the device the material is kept at this position for a period of 2 min. After this period, the piston is moved upwards at a speed of 10 mm/min and the force required for this upwards moving is measured.

Preferably, the polyurethane polymer and the device thereof have a tissue-adhesive strength of at least 0.5 N, more preferably at least 0.75 N, most preferably at least 1 N as determined by the above-described method.

A further advantage of the polyurethane polymers and devices thereof, is their favorable sealant properties. The polyurethane polymers and devices thereof are well resistant to bile, gastric juices and other bodily fluids such that the seal tissue for the time required for the tissue to heal. The tissue-adhesive polyurethane polymer and devices can be used to prevent or limit intra and post-surgical bleeding and leakage of bodily fluids. For instance, after hepatobiliary and pancreatic surgery, bleeding and loss of other fluid is limited or even prevented.

The biodegradable tissue-adhesive polyurethane polymer and device thereof can thus be used in a method for treatment of a human or animal body. Examples of preferred applications of the device are methods of treating or preventing bodily fluid leakage, cranial surgery and/or organ surgery such a liver, hepatobiliary and pancreas (HPB), kidney, bladder, lungs, gastrointestinal, ear, nose, throat, urological, or cardiovascular surgery by sealing the leaking tissue.

For the purpose of clarity and a concise description features are described herein as part of the same or separate embodiments, however, it will be appreciated that the scope of the invention may include embodiments having combinations of all or some of the features described.

The invention may be illustrated by the following examples

EXAMPLE 1

A pre-functionalized polymer in accordance with the present invention was prepared as follows.

A prepolymer (50 g, 0.025 mol, 2000 g/mol) was synthesized from DL-lactide and ε-caprolactone using PEG1000 as an initiator and stannous octoate as a catalyst at a temperature of 140° C. for 14-17 days. The prepolymer was subsequently reacted with 10 equivalents of 1,4-butanediisocyanate (35 g, 0.25 mol) at a temperature of 70° C. for 4 h. The excess of 1,4-butanediisocyanate was removed using a vacuum distillation (<0.02 mbar, 16 h, 100° C.).

The isocyanate concentration in the prepolymer [NCO] (mmol/g) was determined using a dibutylamine titration in which the macrodiisocyanate was reacted with an excess of di-N-butylamine. The unreacted amine was titrated back with an aqueous hydrochloric acid solution. Chain extension was performed in the solvent 1,4-dioxane at an [NCO] of 0.60 mmol/g. This [NCO] was achieved by dilution of the macrodiisocyanate. 2,2-Bis(hydroxymethyl)propionic acid (3.35 g, 0.025 mol) was added to the reaction mixture at a temperature of 90° C. The progress of the reaction was followed by the increase in viscosity and decrease in [NCO] (FT-IR). The reaction became viscous over time. When the reaction mixture became too viscous, small amounts of 1,4-dioxane were added to avoid gelation of the reaction mixture. The reaction was terminated at complete conversion of the residual NCO groups.

EXAMPLE 2

Other pre-functionalized polymers in accordance with the present invention were prepared, by following the procedure of Example 1. The prepolymers were prepared from different monomers (lactide/caprolactone, trimethylenecarbonate, glycolide) and initiators (diethylene glycol, 1,4-butanediol, 1,6-hexanediol, polyethylene glycol). The monomer ratio and molecular weight of the prepolymer were between 500-5000 g/mol. These prepolymers were converted into a macrodiisocyanate using different diisocyanates. Examples of the diisocyanates that were used are: 1,4-butanediisocyanate, 1,6-hexanediisocyanate, 1,8-octanediisocyanate, lysinediisocyanate, isophoronediisocyanate. The macrodiisocyanate was then chain extended with bis(hydroxymethyl) propanoic acid, tartartic acid or citric acid.

EXAMPLE 3

Polyurethane polymers of the present invention was prepared as follows. The pre-functionalized polymer from example 1 and 2, N-hydroxysuccinimide (7.19 g, 0.0625 mol) and DCC (12.89 g, 0.0625 mol). were dissolved in 800 mL of 1,4-dioxane. After stirring overnight at room temperature, the precipitated dicyclohexylurea was removed by vacuum filtration. The solvent was removed using a rotation evaporator. The crude product was redissolved in ethyl acetate. Additional urea byproducts were removed and the filtered solution was then precipitated from an excess of methyl tert-butyl ether (TBME) (10:1) which has been cooled in an ice bath prior usage. Subsequently, the crude product was again dissolved in ethyl acetate and precipitated using TBME. The solvents were removed using a rotation evaporator to yield the final NHS functionalized polyurethane.

EXAMPLE 4

Figure 1:
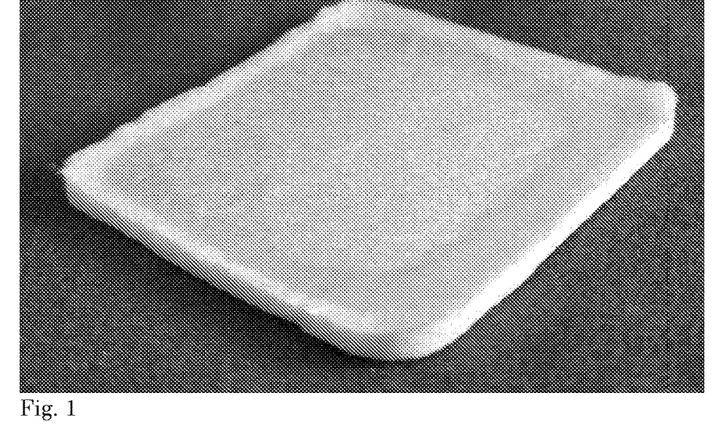
FIG. 1 depicts a biodegradable tissue-adhesive medical device in the form of a foam.

A biodegradable tissue-adhesive medical devices in the form of a foam were prepared by casting a diluted polymer solution with a polymer concentration of 5 wt % in 1,4-dioxane and a cyclohexane concentration of 2 wt % cyclohexane (described in example 3) on top of a frozen polyurethane solution without tissue reactive groups which has a polymer concentration of 5 wt % in 1,4-dioxane and a cyclohexane concentration of 2 wt %. The combined layers were then frozen in a freezer at approximately −18° C. overnight and subsequently freeze-dried overnight. The device depicted in FIG. 1 was obtained.

EXAMPLE 5

A biodegradable tissue-adhesive medical device in the form of a bi-layered foam was prepared from two different polyurethanes (A and B).

Polyurethane (A) which is used as a carrier of the tissue adhesive material (B) is prepared in three steps. A prepolymer (50 g, 0.025 mol, 2000 g/mol) was synthesized from DL-lactide and ε-caprolactone using PEG1000 as an initiator and stannous octoate as a catalyst at a temperature of 140° C. for 14-17 days. The prepolymer was subsequently reacted with 10 equivalents of 1,4-butanediisocyanate (35 g, 0.25 mol) at a temperature of 70° C. for 4 h. The excess of 1,4-butanediisocyanate was removed using a vacuum distillation (<0.02 mbar, 16 h, 100° C.).

The isocyanate concentration in the prepolymer [NCO] (mmol/g) was determined using a dibutylamine titration in which the macrodiisocyanate was reacted with an excess of di-N-butylamine. The unreacted amine was titrated back with an aqueous hydrochloric acid solution. Chain extension was performed in the solvent 1,4-dioxane at an [NCO] of 0.60 mmol/g. This [NCO] was achieved by dilution of the macrodiisocyanate. BDO-BDI-BDO block (8.01 g, 0.025 mol) was added to the reaction mixture at a temperature of 90° C. The progress of the reaction was followed by the increase in viscosity and decrease in [NCO] (FT-IR). The reaction became viscous over time. When the reaction mixture became too viscous, small amounts of 1,4-dioxane were added to avoid gelation of the reaction mixture. The reaction was terminated at complete conversion of the residual NCO groups. The polymer was diluted with 1,4-dioxane until a concentration of 5 wt % was obtained, 2 wt % cyclohexane was added and 12.5 mL of this solution was poured into a 5×5×1 cm Teflon mould and frozen in a freezer at approximately −18° C. overnight.

Figure 2:
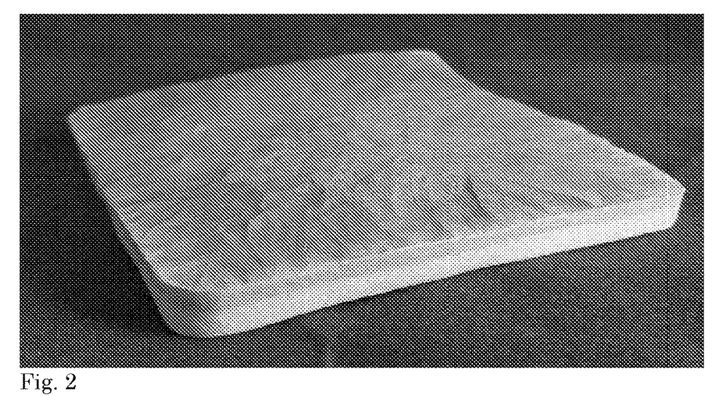
FIG. 2 depicts a biodegradable tissue-adhesive medical device in the form of a bi-layered foam.

Polymer B (Tissue adhesive polymer described in example 3) was diluted until 5 wt % in 1,4-Dioxane. 2 wt % of cyclohexane was added and 12.5 mL of this solution was poured on top of the frozen first layer containing polymer A and frozen in a freezer at approximately −18° C. overnight. The 5×5×1 cm Teflon mould containing the bilayered frozen polymer solutions was freeze-dried overnight. The device depicted in FIG. 2 was obtained.

EXAMPLE 6

Figure 3:
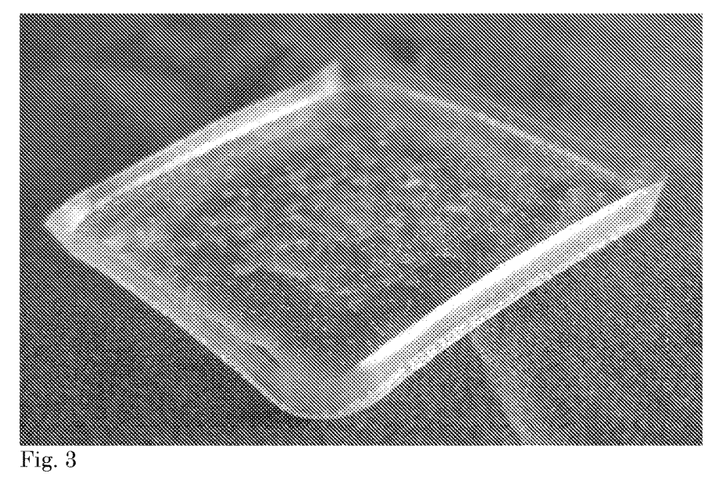
FIG. 3 depicts a biodegradable tissue-adhesive medical device in the form of a sheet.

A biodegradable tissue-adhesive medical device in the form of a sheet was prepared by casting a polyurethane solution (with a concentration of 5 wt %) without tissue adhesive groups into a mold. The solvent (chloroform) was allowed to evaporate at room temperature overnight to obtain a polymer sheet. A 5 wt % solution of the polymer described in example 3 in 1,4-dioxane was poured on top of the sheet and the combined layers were frozen in a freezer at a temperature of −18° C. overnight. Subsequently, the entire mold was freeze-dried for 24 h, to obtain a biodegradable tissue adhesive sheet, which is depicted in FIG. 3.

EXAMPLE 7. IN VITRO TEST METHOD FOR DETERMINING TISSUE-ADHESIVE STRENGTHS

The tissue-adhesive strengths of the foam devices (according to example 1) of the pre-functionalized and polyurethane polymers as prepared in previous were determined as follows.

Figure 4:
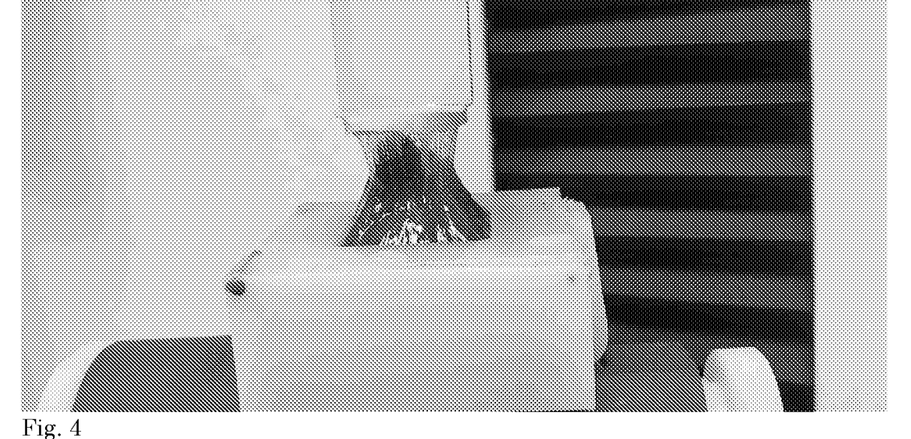
FIG. 4 illustrates an apparatus and method for measuring the tissue-adhesive strength of foam according to Example 1.

Bovine liver tissue is placed inside a Teflon™ box with an opening on top. The foam device comprising the pre-functionalized or polyurethane polymer is attached to a piston using double sided tape. By using the piston, the foam device is pressed onto the liver tissue at a speed of 10 mm/min until a force of 10N has been reached. At this point, the piston with the device the material is kept at this position for a period of 2 min. After this period, the piston is moved upwards at a speed of 10 mm/min and the force required for this upwards moving is measured. FIG. 4 illustrates this method.

Figure 5:
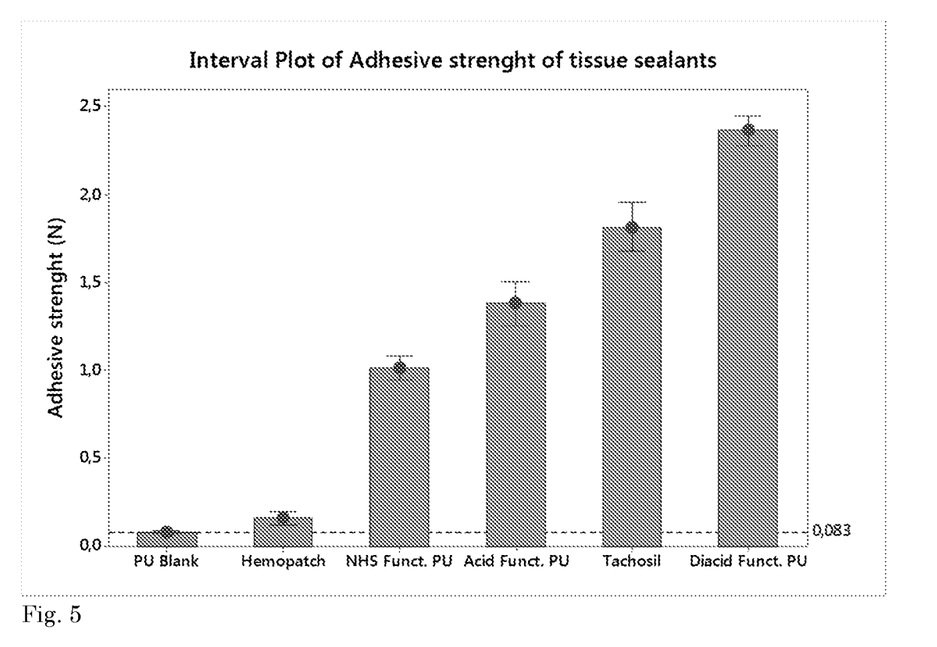
FIG. 5 is a graph of adhesive strength.

The results are provided in FIG. 5.

COMPARATIVE EXAMPLE 1

The adhesive strengths of the polymers of the present invention were compared with commercially available tissue-adhesive materials under the tradenames Hemopatch™ and Tachosil™ in the method according to Example 7.

The results are provided in FIG. 5.

The invention claimed is:

1. A biodegradable tissue-adhesive polyurethane polymer comprising at least one amorphous segment and at least one polyurethane segment, wherein at least one of said polyurethane segment comprises a tissue-reactive functional group, wherein the tissue-reactive functional group is an activated ester, an acid chloride, an anhydride, p-nitrophenyl carbonate, an epoxide, an isocyanate, a vinyl sulfone, maleimide, o-pyridyl-disulfide, or a thiol or combinations thereof, wherein the biodegradable tissue-adhesive polyurethane polymer is of formula (I)

(I)

wherein R is one or more aliphatic polyesters, polyether esters, polyethers, poly(anhydrides) and/or polycarbonates, and optionally at least one R comprises a hydrophilic segment; R' is a $C_2$-$C_8$ alkylene, optionally substituted with $C_1$-$C_{10}$ alkyl or $C_1$-$C_{10}$ alkyl groups substituted with halides or protected S, N, P or O moieties and/or comprising S, N, P or O in the alkylene chain; $R^f$ is a functionalized chain extender substituted with the tissue-reactive functional group; $R^e$ is a chain extender, Q is a urethane; p is an integer from 5-500; n plus m equal 1; and n is not 0.

2. The biodegradable tissue-adhesive polyurethane polymer according to claim 1, wherein the activated ester is selected from the group consisting of a thioester, a perfluoroalkyl ester, a pentafluorophenol ester, and a N-hydroxysuccinimide ester or a derivative thereof.

3. The biodegradable tissue-adhesive polyurethane polymer according to claim 1, wherein the functionalized chain extender ($R_f$) and the chain extender ($R^e$) independently comprise a $C_2$-$C_8$ alkylene or alkyl, a (poly)urethane group, a (poly)ester, a (poly)lactide or a (poly)ether, and wherein, the tissue-reactive functional group ($R_f$) is substituted with a $C_1$-$C_{10}$ hydrocarbon comprising the tissue-reactive functional group.

4. A pre-functionalized biodegradable polyurethane polymer suitable for the preparation of the polyurethane polymer according to claim 1, said pre-functionalized polyurethane polymer being of the formula (II)

wherein R is one or more aliphatic polyesters, polyether esters, polyethers, poly(anhydrides) and/or polycarbonates, and optionally at least one R comprises a hydrophilic segment; R' is a $C_2$-$C_8$ alkylene, optionally substituted with $C_1$-$C_{10}$ alkyl or $C_1$-$C_{10}$ alkyl groups substituted with halides or protected S, N, P or O moieties and/or comprising S, N, P or O in the alkylene chain;

$R^e$ is a chain extender, Q is a urethane; p is an integer from 5-500; n plus m equal 1; and n is not 0; and wherein $R^x$ is a pre-functionalized chain extender at least substituted with a $C_1$-$C_{10}$ hydrocarbon comprising a carboxylic acid, nitrile, isonitrile or optionally protected S, N, P or O.

5. A method for the preparation of a pre-functionalized biodegradable polyurethane polymer according to claim 4, said method comprising chain extending a pre-polymer with a chain extender substituted with a pre-reactive functional group and optionally a chain extender.

6. A method for the preparation of the biodegradable tissue-adhesive polyurethane comprising providing the pre-functionalized biodegradable polyurethane polymer according to claim 5, followed by the conversion of the pre-reactive functional group to the tissue-reactive functional group.

7. The method according to claim 6, wherein the pre-reactive functional group is a carboxylic acid, the tissue-reactive functional group is an activated ester and the conversion of the pre-reactive functional group to the tissue-reactive functional group comprises coupling of an activated alcohol with the carboxylic acid.

8. A biodegradable tissue-adhesive medical device comprising the polyurethane polymer according to claim 1.

9. The biodegradable tissue-adhesive medical device according to claim 8 having the structure of a sheet, foam, stent, tube or gel.

10. A method for treatment of a human or animal body comprising adhering the biodegradable tissue-adhesive polyurethane polymer according to claim 1 to tissue of the human or animal body to seal the tissue.

11. A method of treating or preventing bodily fluid leakage, cranial surgery and/or organ surgery such a liver, hepatobiliary and pancreas (HPB), kidney, bladder, lungs, gastrointestinal, ear, nose, throat, urological, or cardiovascular surgery in a human or animal comprising adhering the biodegradable tissue-adhesive polyurethane polymer according to claim 1 to tissue of the human or animal body to seal the tissue.

12. The biodegradable tissue-adhesive polyurethane polymer according to claim 1 wherein n/m is at least 0.5.

13. The biodegradable tissue-adhesive polyurethane polymer according to claim 1 wherein n/m is at least 0.75.

14. The biodegradable tissue-adhesive polyurethane polymer according to claim 1, wherein the functionalized chain extender ($R_f$) and the chain extender ($R^e$) independently comprise a $C_2$-$C_8$ alkylene or alkyl.

15. The pre-functionalized biodegradable polyurethane polymer of claim 4 wherein the chain extender ($R^e$) comprises a $C_2$-$C_8$ alkylene or alkyl.

* * * * *

UNITED STATES PATENT AND TRADEMARK OFFICE
CERTIFICATE OF CORRECTION

PATENT NO. : 11,129,920 B2
APPLICATION NO. : 16/089610
DATED : September 28, 2021
INVENTOR(S) : Martin Franke Tooren et al.

Page 1 of 1

It is certified that error appears in the above-identified patent and that said Letters Patent is hereby corrected as shown below:

On the Title Page

Column 1, Item (73) Assignee:
Delete "Polygames" and insert --Polyganics--

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*